US012797454B2

(12) United States Patent
Deisseroth

(10) Patent No.: US 12,797,454 B2
(45) Date of Patent: Nov. 17, 2026

(54) mRNA VACCINE DESIGN USING MULTIPLE INTERACTING IMMUNO-STIMULATORY PATHWAYS, FOR CANCER AND INFECTIOUS DISEASES

(71) Applicant: MicroVAX, LLC, Warrenton, VA (US)

(72) Inventor: Albert B. Deisseroth, Potomac, MD (US)

(73) Assignee: MicroVAX, LLC, Warrenton, VA (US)

( * ) Notice: Subject to any disclaimer, the term of this patent is extended or adjusted under 35 U.S.C. 154(b) by 832 days.

(21) Appl. No.: 18/163,333

(22) Filed: Feb. 2, 2023

(65) Prior Publication Data

US 2023/0241193 A1 Aug. 3, 2023

Related U.S. Application Data

(60) Provisional application No. 63/306,140, filed on Feb. 3, 2022.

(51) Int. Cl.
*A61K 39/00* (2006.01)
*A61K 9/00* (2006.01)

(52) U.S. Cl.
CPC .... *A61K 39/001196* (2018.08); *A61K 9/0019* (2013.01); *A61K 2039/53* (2013.01)

(58) Field of Classification Search
CPC .......... A61K 39/001196; A61K 9/0019; A61K 2039/53; A61K 9/5123; A61K 39/0011
See application file for complete search history.

(56) References Cited

U.S. PATENT DOCUMENTS

| | | | | |
|---|---|---|---|---|
| 8,119,117 | B2 | 2/2012 | Deisseroth | |
| 8,299,229 | B2 | 10/2012 | Tang | |
| 9,533,036 | B2 | 1/2017 | Tang | |
| 10,130,667 | B1 * | 11/2018 | Deisseroth | C12N 15/86 |
| 2012/0128656 | A1 | 5/2012 | Har-Noy | |
| 2020/0046820 | A1 | 2/2020 | Deisseroth | |

OTHER PUBLICATIONS

Bereta, M et al. "Immune properties of recombinant vaccinia virus encoding CD154 (CD40L) are determined by expression of virally encoded CD40L and the presence of CD40L protein in viral particles". Cancer Gene Therapy, vol. 11 (2004), pp. 808-818. (Year: 2004).*

McNamara, M.A. et al. "RNA-based vaccines in Cancer Immunotherapy". Journal of Immunology Research, vol. 2015 (2015), ID: 794528; http://dxdoi.org/10.1155/2015/794528. (Year: 2015).*

Pruitt, S.K. et al. "Enhancement of anti-tumor immunity through local modulation of CTLA-4 and GITR by dendritic cells". European Journal of Immunology, vol. 41 (2011), pp. 3553-3563. (Year: 2011).*

Bridle, B.W. et al. "Potentiating cancer immunotherapy using an oncolytic virus". Molecular Therapy, vol. 18, No. 8 (2010), pp. 1430-1439. (Year: 2010).*

Xiang, R. et al. "A dual-function DNA vaccine encoding Carcinoembryonuc Antigen and CD40 Ligand trimer induces T cell-mediated protective immunity against colon cancer in Carcinoenbryonic Antigen-transgenic mice". The Journal of Immunology, vol. 167 (2001), pp. 4560-4565. (Year: 2001).*

Fanslow, W.C. et al. "Structural characteristics of CD40 ligand that determine biological function". Seminars in Immunology, vol. 6 (1994), pp. 267-278. (Year: 1994).*

Gupta, S. et al. "A multi-trimeric fusion of CD40L and gp100 tumor antigen activates dendritic cells and enhances survival in a B16-F10 melanoma DNA vaccine model". Vaccine, vol. 33 (2015), pp. 4798-4806. (Year: 2015).*

Marino M. et al. Skeletal muscle cells: from local inflammatory response to active immunity. Gene Therapy (2011) vol. 18: pp. 109-116.

Liang F. and Lore K. Local innate immune responses in the vaccine adjuvant-injected muscle. Clinical & Translational Immunology (2016) 5,e74, 7 pages.

Ziemkiewicz N. The role of innate and adaptive immune cells in skeletal muscle regeneration. International Journal of Molecular Sciences (MDPI) 2021, vol. 22, 3265, 26 pages.

Kang S-M. and Compans R.W. Host responses from innate to adaptive immunity after vaccination: molecular and cellular events. Mol. Cells. vol. 27: pp. 5-14 (2009).

Bonomo A.C. et al. Crosstalk Between Innate and T Cell Adaptive Immunity With(in) the Muscle. Frontiers in Physiology. Review published: Sep. 18, 2020, 11 pages.

(Continued)

*Primary Examiner* — Nancy J Leith
*Assistant Examiner* — Alexandra Geraldine Dace Denito
(74) *Attorney, Agent, or Firm* — Jacob Frank; Glenn Snyder

(57) ABSTRACT

An immunotherapeutic mRNA vaccine comprises a first translation unit comprising a secretable first fusion protein comprising a co-stimulatory molecule fused to a first TAA, adapted to generate a first TAA specific adaptive immune response by way of a first immunostimulatory pathway. The immunotherapeutic mRNA vaccine also comprises a second translation unit comprising a non-secretable second fusion protein comprising an identical co-stimulatory molecule fused to a second TAA identical to the first TAA, adapted to generate a second TAA specific adaptive immune response by way of a second immunostimulatory pathway, whereby the at least two immune response interact at one or more locations downstream to amplify the first TAA specific adaptive immune response.

15 Claims, 1 Drawing Sheet

(56) References Cited

OTHER PUBLICATIONS

Tan T. et al. A phase I study of an adenoviral vector delivering aMUC1/CD40-ligand fusion protein in patients with advanced adenocarcinoma. Nature Communications published online Oct. 28, 2022, 11 pages.
Kobiyama K. and Ishii K. Making innate sense of mRNA vaccine adjuvanticity. Nature Immunology, vol. 23: pp. 474-476 (2022).
Li C. et al. Mechanisms of innate and adaptive immunity to the Pfizer-BioNtech BNT 162b2 vaccine. Nature Immunology, vol. 23: pp. 543-555 (2002).
Tahtinen S. et al. IL-1 and IL-1ra are key regulators of the inflammatory response to RNA vaccines. Nature Immunology, vol. 23: pp. 532-542 (2002).
Lan J. et al. Structure of the SARS-COV-2 spike receptor-binding domain bound to the ACE2 receptor. Nature 581: pp. 215-220, (2020).
Zhang, L. et al. An adenoviral vector cancer vaccine that delivers a tumor-associated antigen/CD40-ligand fusion protein to dendritic cells. PNAS, vol. 100: pp. 15101-15106, (2003).
Tang, Y. et al. Multistep process through which adenoviral vector vaccine overcomes anergy to tumor-associated antigens. Blood, 104: pp. 2704-2713, (2004).
Tang Y. et al. Vector Prime/Protein Boost Vaccine That Overcomes Defects Acquired during Aging and Cancer. Journal of Immunology 177: pp. 5697-5707, (2006).
Deisseroth A. et al. TAA/ecdCD40L adenoviral prime-protein boost vaccine for cancer and infectious diseases. Cancer Gene Therapy advance online publication, Dec. 14, 2012; 5 pages.
International Search Report and Written Opinion issued for the corresponding international application No. PCT/US2023/061805, mailed May 24, 2023, 8 pages.
P. Aukrust et al. "Enhanced levels of soluble and membrane-bound CD40 ligand in patients with unstable angina, Possible reflection of T lymphocyte and platelet involvement in the pathogenesis of acute coronary syndromes." Circulation, Aug. 10, 1999; pp. 614-620.
T. Elmetwali et al. "CD40L membrane retention enhances the immunostimulatory effects of CD40 ligation." Scientific Reports, Nature; (2020); 10:342, 15 pages.
Xiang R. et al.: "A Dual-Function DNA Vaccine Encoding Carcinoembryonic Antigen and CD40 Ligand Trimer Induces T Cell-Mediated Protective Immunity Against Colon Cancer in Carcinoembryonic Antigen-Transgenic Mice", The Journal of Immunology, vol. 167, No. 8, Oct. 15, 2001, pp. 4560-4565.
Kikuchi T. et al.: "Dendritic Cells Modified to Express CD40 Ligand Elicit Therapeutic Immunity Against Preexisting Murine Tumors", Blood, vol. 96, No. 1, Jul. 1, 2000, pp. 91-99.

* cited by examiner mRNA VACCINE DESIGN USING MULTIPLE INTERACTING IMMUNO-STIMULATORY PATHWAYS, FOR CANCER AND INFECTIOUS DISEASES

CROSS-REFERENCE TO RELATED APPLICATION

This application claims priority and benefit under 35 U.S.C. § 119 (e) to U.S. Provisional Application No. 63/306,140 filed Feb. 3, 2022, the disclosure of which is hereby incorporated by reference herein in its entirety.

FIELD OF THE INVENTION

The present invention relates to enhancing the body's immune system, such as amplifying an immune response against cancer and infectious diseases.

SUMMARY OF THE INVENTION

In accordance with exemplary embodiments, a novel messenger RNA (mRNA) vaccine strategy is provided. The vaccine, consistent with various implementations, may utilize multiple interacting immunostimulatory pathways to induce a potent and robust innate, adaptive, humoral and cellular immune response against target associated antigens (TAA) linked with infectious diseases or with cancer. In a preferred vaccine embodiment, fragments of these target associated antigens (TAA) are connected to the extracellular domain (ecd) or to the transmembrane domain (TMD) which is attached in turn to the ecd of the immunostimulatory CD40 ligand (CD40L) molecule in the form of two fusion proteins that are structurally distinct, where each fusion protein is encoded in mRNA forming at least two separate translation units on a single mRNA molecule, to comprise at least (i) a first translation unit (TU #1) which encodes a first sig-TAA/ecdCD40L fusion protein which is secretable by virtue of it not having any amino-acid sequences which could be considered as transmembrane domain (TMD) sequences (which is referred to as the secretable, "prime" or extracellular pathway), and (ii) a second translation unit (TU #2) which encodes a second fusion protein (TAA/TMD/CD40L) which is non-secretable by virtue of its having amino-acid sequences considered as TMD sequences (referred to as the non-secretable, "boost" or intracytoplasmic pathway), resulting after IM administration, in the activation of at least two or more distinct immuno-stimulatory pathways that interact in an auto-stimulatory fashion.

The overall interaction of two or more immunostimulatory pathways which are initiated by a single vaccination, induces high and prolonged levels of innate, adaptive, humoral and cellular immune responses. This is generated by the interaction of multiple sites of cellular activation and cytokine release, thus generating auto-stimulatory cross-talk of the protein products downstream of translation units TU #1 and TU #2, against a common TAA linked with either an infectious disease or cancer.

I. INTRODUCTION: THE MRNA IMMUNOTHERAPEUTIC VACCINE

Messenger RNA (mRNA) technology rather than DNA technology is frequently being chosen because mRNA technology has certain advantages over DNA vaccines, including reduced time and expense for manufacturing, which can result in a product reaching the marketplace sooner.

The single stranded mRNA vaccine molecule shown in FIG. 1, carries a translation unit which could encode a sig-TAA/ecdCD40L fusion protein, is generally encapsulated in lipid nano-particles (LNPs) or lipid micro-particles (LMPs) to protect the mRNA from being destroyed by nucleases. Once this LMP or LNP encapsulated mRNA vaccine is injected (usually into muscle) and passes through the plasma membrane of antigen presenting cells (APCs) or APC like cells (such as resident facultative APCs, e.g. myoblasts) into the intracytoplasmic compartment of the APC, the mRNA is released from the LMP or LNP, and the translation units are translated into a fusion protein vaccine.

RNA vaccines/compositions have been shown to have advantages over DNA viral vaccines with respect to the ease, rapidity and lower cost with which the manufacturing process can be carried out. The mRNA vaccines need to be stored as a frozen solution to keep the product stable for long term storage. In addition, chemical modifications of the nucleic acid building blocks of the mRNA are carried out in order to lessen the inflammatory side effects of the injected mRNA vaccine. However, it is believed that mRNA vaccines may initially induce an immune response that is greater in magnitude than is the case with viral DNA expression vectors. On the other hand, the level of the immune response may persist for a shorter period of time in mRNA expression vectors. Therefore, there may be a need for "boosting" or re-induction of the immune response with additional vaccinations so that the fusion protein vaccine will persist at high levels of effectiveness for longer periods of time.

II. APPLICANT'S PRIOR WORK PREDATING THE INVENTION

Figure 1:
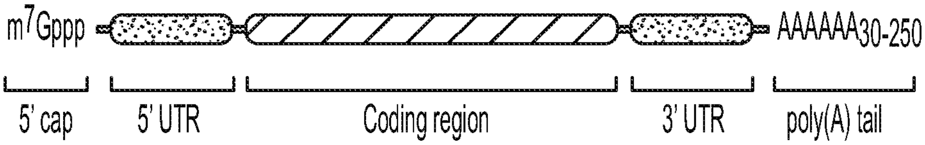
FIG. 1 is a representation of the conventional structural elements of a mRNA vaccine depicting a coding region containing a disease antigen to be targeted.

The original MicroVAX vaccine was an Ad-sig-TAA/ecdCD40L adenoviral expression vector DNA vaccine, where the sig is an intracellular secretory trafficking signal, and the TAA is the target associated antigen (TAA) on or associated with the cancer cell or infectious agent. This vaccine was designed to promote the uptake of the TAA/ecdCD40L fusion protein by dendritic cells by binding of the ecdCD40L end of the sig-TAA/ecdCD40L fusion protein to the CD40 receptors on the antigen presenting or dendritic cells), that then lead to the presentation of the TAA fragments on the Class I and Class II MHC complexes on the surface of the dendritic cell.

III. ABBREVIATIONS—DEFINITIONS

"TMD" or "TM": means the transmembrane domain of the non-secretable

TAA/TMD/ecdCD40L fusion protein could be a segment comprising the entire TMD or a significant portion thereof (in a preferred embodiment), the CD40L transmembrane domain being about 23 amino acids in length. Alternatively, the TMD could be the transmembrane domain of the TAA (Targeted Associated Antigen), if present, assuming this is functionally suitable for a particular therapeutic situation at hand. The transmembrane domain of human CD40L is 23 AA, where the transmembrane domain is in positions 23-46 of CD40L which total AA is 261 AA in length. See U.S. Pat. No. 8,119,117 in which Applicant is a co-inventor, which patent is hereby incorporated herein by reference.

"disease": may be cancer or an infectious disease.

"TAA": target associated antigen or tumor associated antigen, associated with the cancer or infectious agent of interest (antigen specific). The TAA could be a segment comprising the entire TAA or a one or more fragments or a significant portion thereof in a preferred embodiment. Examples of TAA overexpressed antigens in various cancers are mucins, CEA and CA-125 antigens.

"sig": secretory sequence.

"(im)" or "IM": means introducing by injection the vaccine into the muscle tissue of the body intra-muscularly although any other route might be used such as subcutaneously, or the like. The administration in the instant case is preferably intra-muscularly.

"CD40L": CD40 ligand which is an immunostimulatory protein, stimulates an innate immune response characterized by release of cytokines which is followed by an adaptive immune response which is antigen specific.

"ecd": extracellular domain could be the entire extracellular domain of human CD40L or a significant segment thereof or even the extracellular domain of another human co-stimulatory molecule such as CD80 and its receptor CD28.

"MUC-1": refers to just one type of a mucin antigen although any other mucin antigen such as MUC-4, MUC-16 may be considered, and any other non-mucin antigen that is overexpressed in one or more cancers such as CEA and CA-125 might be readily employed for use in the current invention.

"AB": means antibody.

"UTR": untranslated region.

"CAP": 5' end of RNA molecule.

"Poly AAAAAA Tail": 3' end of RNA molecule.

"LMP": lipid microparticle: RNA vaccine wrapped in lipid microparticles.

"LNP": lipid nanoparticle: RNA vaccine wrapped in lipid nanoparticles.

"APCs": Antigen Presenting Cells.

TU or TLU: means a Translation Unit-a basic unit of compilation or a single source file.

"mRNA": messenger RNA.

"disease": means cancer or infectious diseases.

"CPIA": Checkpoint Inhibitory Antibody. Examples of checkpoint inhibitory antibodies are PD-1, PD-L1, PD-L2 and CTLA-4.

"dosing amount": Reasonable or effective amounts of dosing level treatments for the cancer and infectious disease areas relating to fusion proteins (TAA/ecdCD40L and TAA-TMD/ecdCD40L), are disclosed in U.S. Pat. Nos. 8,119,117; 8,299,229 and 9,533,036, in each of which the inventor of the present application is a co-inventor, and which patents are hereby incorporated herein by reference.

"effective amount": means an amount of an anti-cancer agent administration and/or treatment according the teachings of the present invention that is effective to generate (or contribute to the generation) of an immune response in the recipient in treating cancer as described herein. The "effective amount" or dose level will depend upon a variety of factors and may vary according to the disorder being treated, the activity of the specific compound, the route of administration, the rate of clearance of the viral vectors, the drugs used in combination or coincident with the viral vectors, the severity of the disorder, the clinical history of the patient, the patient's age, body weight, sex, diet, physical condition, and/or general health, duration of treatment, and so forth. The effective amount could be more or less than the specified amounts used in the experiment or related experiments and depend upon the considerations taken into account to determine the therapeutically effective amount. Various general considerations are taken into account in determining the therapeutically effective amount are known to those of skilled in the art and are described, e.g. in Gilman et al eds., Goodman and Gilman's "The Pharmacological Basis of Therapeutics," Pergamon Press, and Remmington's "Pharmaceutical Sciences," Mack Publishing Co., Easton, PA.

"combination therapy", "combined treatment" or "in combination": means at least a vaccine and checkpoint inhibitor treatment and/or some other form of antibody or drug, at the same time and/or at different times, within a prescribed time period. The combination therapy could also be an alternate form of therapy such as chemotherapy or radiation therapy.

"checkpoint inhibitor" and/or "antibody": means any one or more of commercial drugs and/or commercial drugs designed, whether or not commercialized and/or sold to administer to an individual (or an animal), for unblocking checkpoints in the body which may prevent the immune system, in part or in whole, from attacking a cancer using the body's T cells, and regardless of how administered.

"PD-1" means one example of a checkpoint inhibitor antibody. Other examples are PD-L1, PD-L2 and CTLA-4

"secretion": is used in reference to the fusion protein TAA/ecdCD40L, and means that the fusion protein includes elements (such as the secretory or signal sequence), that cause secretion of the TAA/ecdCD40L fusion protein to occur, as opposed to an element such as a transmembrane domain of a cell that does not allow secretion to occur.

"antigen": means broadly any antigen or portion thereof to which a human, mammal, bird or other animal can generate an immune response. Antigen as used herein refers broadly to a molecule that contains at least one antigenic determinant to which the immune response may be directed. The immune response may be cell-mediated, humoral or both.

"transcription unit": in vitro or in vivo system in which a DNA template is converted into coding RNA.

"translation unit" or "Translation Unit": in vitro or in vivo system in which an mRNA template is converted into a polypeptide or protein.

"APC" means antigen presenting cells, any of various cells (such as a dendritic cell, macrophage, or B cell) that take up and process an antigen into a peptide fragment which when displayed at the cell surface in combination with a molecule of the major histocompatibility complex is recognized by and serves to activate cells of the immune system (such as helper T cells or cytotoxic T cells).

"MHC" means Major Histocompatibility Complex, an important molecule during the recognition of antigens (foreign substances). They are considered to be a set of cell surface proteins which basically function to bind with foreign antigens to present them on either of the T cell types: Class II MHC bound TAA peptides on APCs are presented to T helper cells ($T_H$) or Class I MHC bound TAA peptides on APCs are presented to the T cell receptor on the cytotoxic T cell ($T_C$).

"MHC Class I" means MHC class I molecules present antigens on the co-receptor molecules known as CD8 which are situated on Tc cells.

"MHC Class II" means molecules present antigens on the co-receptor CD4 which are situated on Tu cells. This is the key difference between MHC Class I and MHC class II.

"cross-talk" means stimulatory interaction between two immunostimulatory proteins, each traveling on separate but in immunostimulatory interactive paths.

"cytokine release" means a condition that may occur after treatment with some types of immunotherapy. Cytokine release syndrome is caused by a large, rapid release of cytokines into the blood from immune cells affected by the immunotherapy. Cytokines are immune substances that have many different actions in the body.

IV. MRNA VACCINE BASIC DUAL TRANSLATION UNIT DESIGN

Figure 2:
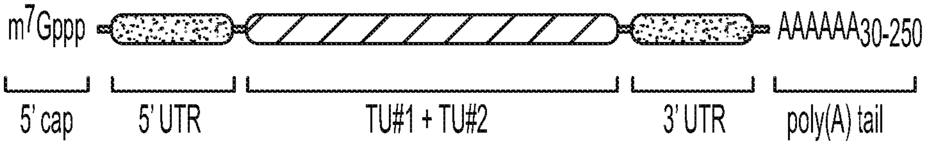
FIG. 2 is a preferred embodiment of the current invention depicting a coding region having two distinct Translation Units TU #1 and TU #2.
Figure 3:
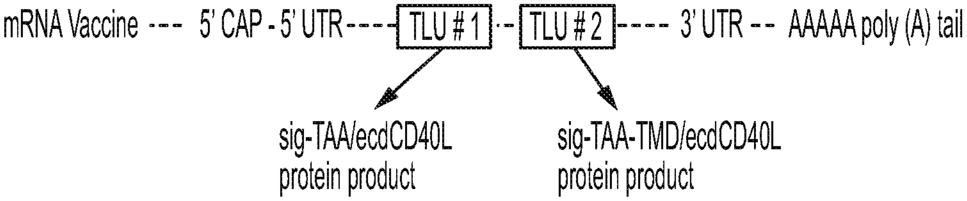
FIG. 3 depicts a preferred embodiment where two similar but structurally distinct fusion proteins (sig-TAA/ecdCD40L and TAA/TMD/ecdCD40L) are encoded as separate translation units in the coding section of a single mRNA vaccine molecule.

Description of Vaccine Comprising Two Translation Units TU #1 and TU #2. The preferred embodiment of the current Invention is a messenger RNA (mRNA) vaccine which has the following components, as shown in FIGS. 2 and 3, for an mRNA composition: 5' CAP-5' UTR-Translation Unit #1 (TU #1) which has a strand of RNA encoding a standard sig-TAA/ecdCD40L secretable fusion protein composition, which is followed by Translation Unit #2 (TU #2) which has a strand of RNA encoding a-TAA/TMD/ecdCD40L (TMD meaning in this preferred embodiment the non-secretable transmembrane domain of CD40L)—which is followed by a 3'UTR-which is followed by a AAAAAA-tail. The RNA vector, once injected into the intracellular compartment in the muscle cells, converts or translates its Translation Units from RNA into protein in the manner described below.

V. PROPHETIC EXAMPLE

This is a preferred embodiment of a costimulatory molecule CD40L depicting two similar but structurally different fusion proteins (TAA/ecdCD40L and TAA/TMD/ecdCD40L), each encoded to form two separate Translation Units in a single mRNA molecule for use as a single vaccine or composition injection.

As a prophetic example, the below listing of events provide first an outline and then a detailed description of two immune response pathways which follows the IM injection of the LNP encapsulated mRNA vaccine.

TU #1 Pathway: Outline of TU #1 Pathway

- Event-1: IM injection of mRNA/LNP vaccine, passage of the LNP encapsulated mRNA vaccine into the intracytoplasmic compartment of APC, release of the mRNA from the LNP
- Event-2: Translation of TU #1 mRNA into sig-TAA/ecdCD40L protein
- Event-3: Secretion of sig-TAA/ecdCD40L to extracellular space.
- Event-4: Binding of sig-TAA/ecdCD40L to CD40 receptor on surface of APC with release of cytokines, activation APC and T cells in both TU #1 and TU #2 pathways.
- Event-5: Uptake of the complex of the sig-TAA/ecdCD40L with the CD40 receptor into vesicular compartment, MHC Class II processing of TAA into presentation peptides (13-18 AA long) which bind to Class II MHC.
- Event-6: Presentation of TAA peptides on Class II MHC.
- Event-7: Recognition of TAA peptides by CD4 ($T_H$) cells with cytokine release and activation of APCs and T cells in both TU #1 and TU #2 pathways.

Detailed Description of TU #1 Pathway:

1. The following Events 1a-1g are triggered by the synthesis of the sig-TAA/ecdCD40L protein from Translation Unit #1 (TU #1). The IM injection of a single strand of mRNA described in Event 1 of the TU #1 Pathway, which is encapsulated in LMP or LNP, into muscle tissue leads to the following events:
   - 1a. Passage or transmigration of the LNP containing mRNA through the plasma membranes of APCs and other APC-like cells (e.g. myoblasts), and into the intracytoplasmic compartments of these cells.
   - 1b. Release of the mRNA strand from the LNP described in Event 2 of the TU #1 Pathway.
   - 1c. Conversion (translation) of the mRNA sequences described in Event 2 of the TU #1 Pathway into the sig-TAA/ecdCD40L fusion protein by translation of the mRNA of TU #1.
   - 1d. Passage (secretion) of the sig-TAA/ecdCD40L fusion protein through the plasma membrane of APCs and other APC like cells (e.g. myoblasts) into the extracellular compartment which secretion is believed to take place for at least a 10 day period as described in Event 3 of the TU #1 Pathway.
   - 1e. As described in Event 4 of the TU #1 Pathway, the binding of the extracellular domain (ecd) of a sig-TAA/ecdCD40L protein to the CD40 receptor on the surface of the APCs and other facultative antigen presenting cells (e.g. myoblasts) triggers an activation of the APCs and induces cytokine release from the activation of APCs and T cells in the TU #1 pathway, and also induces activation of the APC in the TU #2 pathway through cross-talk. This is called: "Cytokine release with activation of APCs and $T_H$ cells in the activation of APCs and $T_H$ cells of TU #1 and APCs and $T_C$ cells of TU #2 through cross-talk in the TU #2 Pathway."
   - 1f. Recognition by TAA specific $T_H$ cell lymphocytes with cytokine release from $T_H$ cells and induction of the expansion of an initial innate and then adaptive immune response TAA specific T cell lymphocytes that results in increases in the levels of TAA specific CD4 $T_H$ cell lymphocytes, as is described in Event 6 of the TU #1 Pathway. This is called "Cytokine release with activation of APCs and $T_H$ cells in the activation of APCs and $T_H$ cells of TU #1 and APCs and T cells of TU #2 through cross-talk at Event 6 in TU #1 Pathway." The recognition of TAA specific peptides on Class II MHC by TAA specific CD4 effector $T_H$ cell results in consequent cytokine release and activation of APCs and TAA specific T cells in both the TU #1 and TU #2 pathways.

TU #2 Pathway: Outline of TU #2 Pathway:

- Event-1: IM injection of mRNA/LNP vaccine, into muscle tissue followed by passage of LNP encapsulated mRNA through plasma membrane of APC into intracytoplasmic compartment of APC, release mRNA from LNP
- Event-2: Translation of TU #2 mRNA into TAA/TMD/ecdCD40L protein.
- Event-3: MHC Class I processing of TAA into presentation peptides followed by binding of TAA peptides 8-9 AA in length.
- Event-4: Presentation of TAA peptides on Class I MHC.

Event-5: Recognition of TAA peptides by CD8 $T_C$ cells with cytokine release and activation of APCs and T cells in both TU #1 and TU #2 pathways.

Detailed Description of TU #2 Pathway:

2. The IM injection of mRNA strand described in Event 1 of the TU #2 Pathway, which is encapsulated in LMP or LNP, into muscle tissue leads to the following events 2a-2e, triggered by synthesis of TU #2 (TAA/TMD/ecdCD40L):

2a. Passage or transmigration of the LNP which contains the mRNA vaccine through the plasma membrane of APCs and other APC-like muscle cells (e.g. myoblasts).

2b. Release of the mRNA from the LNP, and conversion of the mRNA of TU #2 into the TAA/TMD/ecdCD40L fusion protein, occurs in the intracytoplasmic compartment, as described in Event 2 of the TU #2 Pathway. (Note: The TAA/TMD/ecdCD40L fusion protein from TU #2 is not secreted from the intracytoplasmic intracellular compartment.) This pathway is called the intracytoplasmic or non-secretable pathway.

2c. Intracytoplasmic MHC "processing" occurs next which reduces the TAA into peptides >8-9 AA long, so they will fit into the binding cleft in the MHC Class I for binding of TAA to Class I MHC in Event 3 of the TU #2 Pathway.

2d. This reduced sizing of the TAA peptides from the vaccine from TU #2 in this processing allows for the binding of TAA presentation peptides from the intracytoplasmic compartment for the TU #2 pathway to Class I MHC protein for eventual presentation on the surface of the plasma membrane of the APC, as described in Event 4 of the TU #2 Pathway.

2e. The next event is the recognition of the MHC Class presented TAA peptides by TAA specific CD8 effector $T_C$ cells which is accompanied by release of cytokines from the APCs and T cells involved in the recognition of TAA specific Class I MHC bound peptides at Event 5 of the TU #2 Pathway. The release of cytokines from the T cells of the TU #2 Pathway activates APCs and T cells in the pathway from TU #2 and these same cytokines activate APCs and T cells from the TU #1 through the interaction of cross-talk from TU #2 with APCs and T cells from TU #2 to TU #1 pathways. This is called "Cytokine release with activation of APCs and T cells in the activation of APCs and $T_C$ cells of TU #2 and APCs and $T_C$ cells of TU #1 through cross-talk at Event 5 of the TU #2 Pathway."

This auto-stimulatory cascade due to multiple events of cytokine release and activation of APCs and T cells results in a further increase of the magnitude and duration or prolongation of the levels of the TAA specific T cell lymphocytes resulting in amplification of the initial adaptive immune response that results in further increases of the previously expanded TAA specific CD8 effector T cells and prolongs the time of their effective time period. This generates a prime-boost sequence effect with a single IM injection of the LNP encapsulated mRNA vaccine.

The introduction of the TMD into the vaccine from TU #2 creates two separate pathways: the secretion and non-secretion pathways. TAA peptides from the vaccine entering the APC from the extracellular pathway are processed and presented by MHC Class II proteins, and TAA peptides from the vaccine that remain in the intracytoplasmic compartment are processed and presented by MHC Class I.

Summary of the TU #1 Pathway: The IM injection of mRNA vaccine encapsulated by a LMP or LNP) induces an initial innate immune response. The next event (see Event 2 of the TU #1 Pathway is the translation of the mRNA of TU #1 into the sig-TAA/ecdCD40L protein product of Translation Unit #1 (secretion or extracellular pathway). Next, the fusion protein from TU #1 is secreted to the extracellular compartment, (Event 3 of the TU #1 Pathway, and then binds to the CD40 receptor, as described by Event 4 of the TU #1 Pathway, on the exterior surface of the APC.

The binding of the sig-TAA/ecdCD40L (product of TU #1) to the CD40 receptor on the surface of the APC (see Event 4 of the TU #1 Pathway) triggers activation of the APC and T cells with cytokine release. The cytokines activate the APCs and T cells on both the TU #1 pathway and through cross-talk the TU #2 pathways. This is followed by uptake of the sig-TAA/ecdCD40L/CD40 receptor complex into the intravesicular compartment of the APC leading to the MHC processing and presentation of TAA fragments on Class II MHC (see Event 6 of the TU #1 Pathway). Next, the TAA fragments bound on MHC Class II complexes are recognized by CD4 T helper cells (see Event 7 of the TU #1 Pathway). This is accompanied by cytokine release and activation of APCs and T cells on the TU #1 pathway and with APCs and T cells of the TU #2 pathway through cross-talk between the two pathways.

Summary of the TU #2 Pathway: Following release of mRNA from the LNP in the intracytoplasmic compartment of the APC, the mRNA of TU #2 is translated into the TAA/TMD/ecdCD40L protein (see Event 2 of the TU #2 Pathway). Next, the MHC Class I processing of the TAA into peptides of 8-9 amino acids in length, as described in Event 3 of the TU #2 Pathway as a prerequisite for binding of the TAA peptides processed by the Class I MHC proteins. As described by Event 4 of the TU #2 Pathway, the TAA processed peptides bound to Class I MHC are presented on the surface of the APC. As shown by Event 5 of the TU #2 Pathway, the TAA are recognized by TAA specific CD8 positive $T_C$ cells. This is accompanied by cytokine release and activation of the APC and T cells of both the TU #1 and TU #2 pathways.

Mechanism of Invention: It is apparent that the pathways generated by the TU #1 and TU #2 are stimulating each other through release of cytokines (Events 4 and 6 of Pathway TU #1 and the release of cytokines at Event 5 in the TU #2 pathway resulting in augmentation of the magnitude of the increase of the TAA specific T cell lymphocytes produced by the binding events leading to presentation of TAA from the vaccine produced from TU #2 and TU #1 respectively on fragments on Class I and Class II MHC. The increase of the magnitude of the immune response with the combination of the vaccine from TU #1 and TU #2 pathways in combination will further result in a prolongation or extension of the time the immune response is elevated above that seen with the treatment with the TU #1 fusion protein alone.

Thus, a single vaccination of the mRNA vaccine encapsulated by LNP triggers the formation of two independent vaccine pathways that are interacting in an auto-stimulatory fashion through the two TAA/CD40L pathways: one with and one without TMD.

APCs: Antigen-presenting cells (APCs) are a heterogeneous group of immunoreactive cells that modulate the cellular immune response by processing and presenting antigens for recognition by different subsets of lymphocytes. Classical APCs include dendritic cells, macrophages, Langerhans cells and B cells. Dendritic cells are considered to have the broadest range of antigen presentation molecules and are necessary for activation of naive T cells. DCs present antigen to both helper and cytotoxic T cells. Myoblasts express MHC genes at baseline and the MHC genes are up regulated in the pro-inflammatory conditions that prevail under the IM injection used for administration of the mRNA LNP vaccine.

Auto-stimulatory Loops: Accordingly, this design of the mRNA vaccine design generates a robust adaptive immune response through the use of at least two or more immune pathways the first of which is secretable, that then leads to the binding of the sig-TAA/ecdCD40L to the CD40 receptor on the surface of APC which in turn leads to cytokine release which enhances further activates the TU #2 as well as the TU #1 pathway, an example of cross-talk/interaction for amplification of the overall immune response generated by way of the two pathways.

The second TU #2 pathway is primarily an intracellular pathway in the intracytoplasmic compartment. The TU #2 on the mRNA is located in the intracytoplasmic compartment where all the translation machinery needed for the conversion from mRNA into the proteins are available. Because of the TMD on the vaccine from TU #2, the TAA from this fusion protein remains in the intracytoplasmic compartment where it is processed (degraded into fragments) and then bound to Class I MHC which carries them to the outside surface of the APC for presentation.

The TAA for the vaccine product of TU #1 is secreted after translation from mRNA into protein and is secreted from the intracytoplasmic compartment from which product of TU #1 is secreted to outside of the APC.

The pathways for both fusion proteins produce signals for cellular activation and cytokine release (see Events 4 and 6 of the TU #1 pathway and Event 5 of the TU #2 pathway). Each of these three cytokine release events lead to amplification of the immune response induced by vaccination for both directions TU #1 to TU #2, as well as from TU #2 to TU #1. This design creates an auto-stimulatory prime boost cycle in both directions for cancer and infectious diseases.

The Targeted/Tumor Associated Antigen (TAA): The TAA could be, for example, a HPV (human papilloma virus E6 or antigen E7 shown in U.S. Pat. No. 8,119,117), or the mucin antigen fragment (MUC-1) (shown in the above referenced U.S. Patent) level of the induced immune response compared to that observed with the TU #1, is hereby incorporated into this application by reference. One might even consider targeting two or more TAAs depending upon the need and considering the particular disease at issue, and whether alone or in combination with one or more other therapies such as, for example, a checkpoint inhibitory antibody (CPIA), other antibody therapy, or chemotherapy and/or radiation therapy.

VI. OTHER EMBODIMENTS & COMBINATIONS

A preferred embodiment of Applicant's invention is to take maximum advantage of the combination of secretable (TU #1 or extracellular) and non-secretable (TU #2 or intracytoplasmic) fusion proteins as two separate components. As outlined above, the increased magnitude of the immune response induced by the combination of TU #1 and TU #2 together as compared to the TU #1 alone will prolong or extend the time that the increased level remains elevated as compares with the TU #1 alone.

The two pathways arise in the fusion protein vaccines encoded in TU #1 and TU #2 are considered "downstream" from the TU #1 and TU #2. Thus, a single mRNA vaccine as a single vaccine delivery mechanism can produce the effect of a multi-injection prime-boost.

If the two fusion protein components are injected separately but sequentially at a common body site, the amplification that arises from the cross-talk between TU #1 and TU #2 would not occur and the overall magnitude of the immune response would be less. In yet a further alternative embodiment, any co-stimulatory protein, other than CD40L, capable of generating a humoral and/or cellular immune response, might be used in the practice of Applicant's current invention, whether in the field of infectious disease or cancer, such as, for example, a stromal interaction molecule 1 (STIM1), or a *listeria* protein Lm-LLO, or the OX-40 and its cognate ligand OX40L co-stimulatory molecule which is a member of the TNF superfamily, and a transmembrane domain may be similarly employed as a TMD fragment similar to the application of Applicants CD40L fusion protein for use as a self-contained prime-boost mRNA immuno-therapeutic regimen (one with the ecd protein fused or combined with solely a TAA fragment, and another with the protein ecd fused or combined with both a TAA fragment and with a TMD fragment).

In yet even a further embodiment of Applicant's invention, the second Translation Unit or even a third Translational Unit TAA/TMD/ecdOX40L fusion protein might include a different co-stimulatory molecule as part of a fusion protein, in combination with the first Translation Unit TAA/ecdCD40L, inasmuch as the TAA segment of this later non-secretable fusion protein would be the only segment of the non-secretable fusion protein that is anchored in but exposed to the extracellular compartment and to the initial adaptive immune response.

Considering that different co-stimulatory molecules, in fact, act at different stages to modulate and control the immune response, the different co-stimulatory molecules depending on their action and function, at different stages can engage one or more additional immune pathways in the body to migrate into or be exposed at the extracellular compartment during distinct time periods, providing for additional boosts to the initial adaptive immune response, to provide for a complementary immunological effect. For example, the OX40 signaling effect is known to affect late proliferation and survival in the T cell effector phase. In such a configuration Translation Unit #1 might be a TAA/ecdCD40L fusion protein whereas Translation Unit #2 might be a TAA/ecdOX40 fusion protein, or TAA/ecdCD40L, where the TAA is a common antigen target of interest such as MUC-1.

Yet in addition to the foregoing example, added as Translation Units #3 and #4, might be the non-secretable version of each of the two latter fusion proteins. In this more complex embodiment due to co-stimulatory molecules acting at different stages together with two of the Translation Units being non-secretable, there could be four immune pathways employed in total, providing a much more enhanced complementary immunological effect. Supplemental to any one or more of the foregoing examples, a suitably selected adjuvant might yet additionally be fused to the secretable and/or non-secretable fusion proteins to further add one or more additional immune pathways and yet additionally advance the efficacy effect and additional prolongation of the body's immune response to a targeted antigen.

An additional third or fourth Translation Unit also might be employed in a situation where there are additional functional objectives such as additional target antigens (different mucins or other target antigens) where each different antigenic fragment would be fused for example, to the extracellular domain of a CD40 ligand and is additionally encoded in the mRNA vaccine as yet two additional separate translation units one with a transmembrane domain and one without a transmembrane domain. A translation unit #3 and/or #4 could, for example, also contain one or more antibodies (other TAA) that might otherwise be administered separately in therapeutic combination treatment, to in effect, even generate additional immune pathways in a patient to more effectively treat the targeted disease such as cancer.

mRNA Vaccine-CPIA and/or VEGF Immunotherapy Combination: In certain diseases, like cancer, as previously noted, it has become recognized that combination therapies of characterized by different modes of treatment can be more effective than any single mode of treatment in fighting this deadly disease. Numerous trials are underway to find effective combinations of therapies with checkpoint inhibitor antibodies ("CPIAs") like PD-1, PD-L1, PD-L2 and CTLA-4, inhibitory antibodies and/or a Bruton's Tyrosine Kinase inhibitor, and/or a Vascular Endothelial Growth Factor (VEGF) antibody (or other growth factor antibody), as these non-targeted antibodies have been found to be more effective when combined with other immunotherapies, especially with targeted immunotherapies.

Further, Applicant is additionally of the belief that a mRNA immunotherapeutic vaccine like that of the instant invention, which has an intrinsic prime-boost effect from an efficacy standpoint and a more prolonged vaccine effectiveness, will even better serve to interface with, for example, CPIAs and/or VEGFs, that may be administered on a two or three-weekly basis, with even less of a possibility of toxicity concerns, as a consequence of the unique single injection prime-boost capability. That such a combination of immunotherapy will provide for yet a more robust and continuous efficacy effect including a prolonged generation of CD8 T cells to kill the cancer cells over an extended period of time, and is believed will further extend the memory B cell and T cell capability of the combination immunotherapy making it yet more immune stimulatory, although it is understood additional prime-boost administrations of the Applicant's current vaccine invention may be additionally administered.

Immune System Correction/Restoration of Immunoreactive Cells:—Such an immunotherapy combination is believed to have many advantages, employing the multiple immune pathways associated with the current invention, such as less toxicity issues, a more robust tumor suppression and efficacy by engaging more natural pathways of an individual's immune system, including but not limited to, enhanced B cell memory extension, reducing even the possible need for multiple injections of the vaccine, and further possibly spacing out, if found advisable, of the intervals for vaccine injection of the patient, as well as perhaps for the immunotherapeutic combination with other molecules such as CPIA and/or VEGF infusion, which when collectively applied could conceivably lessen the overall toxicity and cost of the patient care and improve the impact on the treatment and the quality of life of the patient and extend survival.

Recently it has been found in an Immunome blood study that Applicant's TAA/ecdCD40L fusion protein vaccine has been found to help correct from both a quantitative and qualitative standpoint a cancer patient's immunoreactive cells in a diseased patient's defective immune system as compared with immunoreactive cells of a normal individuals healthy immune system (see Nature Communications publication by Tira J. Tan et al, dated Oct. 28, 2022, entitled "A phase 1 study of an adenoviral vector delivering a MUCI/CD40-ligand fusion protein in patients with advanced adenocarcinoma"), which is incorporated herein by reference.

In this publication, it was found that Applicant's immunotherapeutic TAA/ecdCD40L fusion protein corrected or restored in varying degrees (with each cancer patient) from a quantitative and qualitative standpoint, the deficient immunoreactive cells of a cancer patient's immune system as compared with a healthy individual's immunoreactive cells. It is believed that, as a consequence, with the use of Applicant's instant invention using multiple immune pathways that such corrective or restoration action of a diseased patient's immunoreactive cells will be even more robust, thereby further enhancing the correction of a cancer patient's immune system in the never-ending fight against cancer.

Some characterize the networking of immunoreactive cells as biological pathways making up a series of actions among molecules in a cell that leads to a certain product or change in the cell and accomplish tasks, for example, it can trigger the assembly of new molecules, such as a fat or protein, turn genes on and off, or spur a cell to move, accomplishing tasks. When multiple biological pathways interact with one another, they form a biological network. These biological pathways control a person's response to the world. For example, some pathways subtly affect how the body processes drugs. Immune pathways are believed to be in essence biological pathways, and their correction or restoration, even if in part, can be important, and Applicant considers an improvement in the TAA/ecdCD40L targeted fusion protein vaccine, as proposed herein, may help in part to further restore both quantitatively and qualitatively, biological pathways/networks which may in part become deficient as a consequence of a person becoming diseased.

As an additional consideration, the current invention can become, for example, a more valuable immunotherapeutic tool when a crisis like the recent COVID-19 viral pandemic comes about, where the instant protein-boost vaccine, using multiple immune pathways and cross-talk amplifying the therapeutic effect of the vaccine, additionally strengthens or reinforces deficient immune systems of those that are immunocompromised (having a weakened immune system) against infection, due to a disease, a medical condition, medication, a biologic agent or for a litany of other reasons, as the immune system is believed to be the best first line of defense against being subject to infection by such viral diseases. In addition, the potential public to be vaccinated, having an understanding that a vaccine to be administered for use against a pandemic like situation would be more likely to readily accept such a vaccine and be less concerned about being vaccinated.

VII. TOXICITY

A major issue with any vaccine that is injected into a human is toxicity and separate from perhaps a single vaccine administration is in cases where several vaccine administrations are necessary or important to the overall recovery especially in the cases of cancer where multiple injections are generally necessary to achieve a positive result which is elimination of cancerous tumor tissue. In such instances due to the nature of the present vaccine format invention involving dual pathways in the body, with careful experimentation, one might possibly reduce the number of microparticle and/or nanoparticles to help diminish toxicity, especially, if an injection is to be made in human muscle. The issue of dose and toxicity of mRNA vaccine chemical modifiers of RNA nucleic building blocks of RNA have been associated with proinflammatory toxicity attributed to the mRNA. Chemical modification of the RNA is required to mitigate this effect. Toxicity due to the LNP is also possible.

The mRNA vaccine described above and/or dual encoding technique, may be administered intra-muscularly, intra-dermally, orally and/or subcutaneously, although intra-muscularly is preferred.

The invention claimed is:

1. An immunotherapeutic mRNA vaccine, for administration to an individual in a single administration of a vaccine adapted to generate a cellular and humoral immune response against a disease by therapeutic stimulation through two or more immunostimulatory interacting pathways, comprising an encoding region having at least two separately encapsulated translation units, comprising:

a first translation unit comprising nucleic acid encoding for a secretable first fusion protein comprising a first co-stimulatory molecule and a first target-antigen, adapted to generate a first target-antigen immune response by way of a MHC Class II immunostimulatory pathway, and a second translation unit comprising nucleic acid encoding for a non-secretable second fusion protein comprising an identical second co-stimulatory molecule to the first co-stimulatory molecule and a second target-antigen identical to the first target-antigen, adapted to generate a second target-antigen immune response by way of a MHC Class I immunostimulatory pathway, wherein said non-secretable second fusion protein includes fragments of a transmembrane domain (TMD) common to the first and second co-stimulatory molecules, wherein said TMD is connected between and to each said second co-stimulatory molecule and said second target-antigen.

2. An immunotherapeutic mRNA vaccine according to claim 1, wherein said fragments of the transmembrane domain member (TMD) are fragments common to a transmembrane domain of the second target-antigen.

3. An immunotherapeutic mRNA vaccine according to claim 1, wherein said MHC Class II and MHC Class I immunostimulatory pathways are adapted to biologically interact in a delayed manner at multiple crosstalk events of cellular activation to amplify and prolong said first and second target-antigen immune responses and induce a cytokine release at each crosstalk event.

4. An immunotherapeutic mRNA vaccine according to claim 1, wherein said MHC Class II and MHC Class I immunostimulatory pathways interact in an auto-stimulatory manner through multiple cross-talk events to amplify and prolong said first and second target-antigen immune responses.

5. A method for manufacturing the immunotherapeutic mRNA vaccine of claim 1 for strengthening an individual's immune system, that is self-amplifying and activates a cytokine release, by:

incorporating in the mRNA vaccine separate first and second translation units (TUs), each TU comprising nucleic acid encapsulated in lipid nanoparticles, adapted when administered, to separately and simultaneously generate immune response pathways that interact through crosstalk;

incorporating, in the first TU, a secretable molecule adapted to generate an MHC Class II binding immunostimulatory pathway; and incorporating, in the second TU, a non-secretable molecule, which is a duplicate of said secretable molecule and additionally includes a transmembrane domain (TMD), adapted to generate an MHC Class I binding immunostimulatory pathway.

6. A method according to claim 5, wherein each of said secretable and non-secretable molecules is structured to comprise a co-stimulatory protein fused to a target antigen and said second TU further comprising fragments of a transmembrane domain of said costimulatory protein.

7. A method according to claim 6, wherein said first and second TUs comprises an extracellular domain (ecd) and an intracellular secretory trafficking signal (sig), and said first TU comprises sig-target-antigen/ecdCD40L and said second TU comprises sig-target-antigen/TMD/ecdCD40L.

8. An immunotherapeutic mRNA composition for administration to a patient in a single vaccine administration, comprising at least two translation units (TUs) each separately wrapped in a single lipid nano-particle to form two separate components for therapeutic use, comprising:

a first translation unit comprising a strand of RNA encoding a secretable sig-TAA/ecdCD40L first fusion protein, adapted through a first immune response pathway for generating a Class II MHC first immune response against the target associated antigen (TAA), a second translation unit comprising strand of RNA encoding a non-secretable sig-TAA/TMD/ecdCD40L second fusion protein, adapted through a second immune response pathway for generating a Class I MHC second immune response against a TAA that is the same TAA as in the first translation unit, and wherein said TMD is common to that of a CD40L and directly connected to the TAA, and wherein upon administration, said second pathway is biologically delayed in an auto-stimulatory manner at multiple crosstalk events to amplify and prolong said Class II MHC and Class I MHC immune responses.

9. An immunotherapeutic mRNA composition according to claim 8, wherein said pathways through their interaction at each of two or more crosstalk events activate a cytokine release.

10. An immunotherapeutic mRNA composition according to claim 8, wherein said TMD is common to that of a transmembrane domain of said TAA instead of a CD40L.

11. An immunotherapeutic mRNA vaccine for delivery in a single administration to a patient, comprising two separate complexes, comprising:

a secretable target-antigen/ecdCD40L complex adapted to induce a first immune response for migration through a first immune response pathway; and a non-secretable target-antigen/TMD/ecdCD40L complex adapted to induce a second immune response for migration through a second immune response pathway;

wherein each of said complexes comprises the same target-antigen, wherein the non-secretable complex enables the target-antigen to remain in a cytoplasmic compartment for processing and binding to Class I MHC, and wherein, upon administration, said pathways are adapted through crosstalk events to amplify and delay in time each of said first and second immune responses, and are further adapted to activate multiple cytokine releases.

12. An immunotherapeutic mRNA vaccine according to claim 11, wherein said TMD is from a transmembrane domain of the target-antigen or from the CD40L.

13. A mRNA immunotherapeutic vaccine for enhancing the immune system of an individual, the mRNA vaccine comprising two separate complexes, comprising:

a secretable complex adapted to induce MHC Class II processing first immune response for migration through a first immune response pathway;

a non-secretable complex adapted to induce MHC Class I processing second immune response for migration through a second immune response pathway;

each of said complexes comprising a same extracellular domain (ecd) of a co-stimulatory protein and a same target-antigen, wherein the non-secretable complex comprises fragments of a transmembrane domain (TMD) located between and connected to each said target-antigen and said ecd.

14. An A mRNA immunotherapeutic vaccine according to claim 13, wherein said co-stimulatory protein is the extracellular domain (ecd) of a co-stimulatory CD40L ligand and the TMD comprises fragments of a transmembrane domain of the CD40L ligand or fragments of a transmembrane domain of the target-antigen, and wherein upon administration of said vaccine to the individual, said first and second immune response pathways interact at each of several crosstalk events to activate a cytokine release.

15. An mRNA immunotherapeutic vaccine according to claim 13, wherein said secretable complex is target-antigen/ecdCD40L and said non-secretable complex is target-antigen/TMD/ecdCD40L, wherein said TMD comprises fragments of a TMD of a CD40L ligand.

* * * * *